(12) United States Patent
Wozney et al.

(10) Patent No.: US 6,620,406 B1
(45) Date of Patent: Sep. 16, 2003

(54) METHODS FOR TREATMENT OF PERIODONTAL DISEASES AND LESIONS USING BONE MORPHOGENETIC PROTEINS

(75) Inventors: John M. Wozney, Hudson, MA (US); Thomas J. Turek, Boston, MA (US)

(73) Assignee: Genetics Institute, LLC., Cambridge, MA (US)

( * ) Notice: Subject to any disclaimer, the term of this patent is extended or adjusted under 35 U.S.C. 154(b) by 0 days.

(21) Appl. No.: 08/379,813

(22) Filed: Jan. 27, 1995

Related U.S. Application Data

(63) Continuation-in-part of application No. 08/208,722, filed on Mar. 8, 1994, now abandoned.

(51) Int. Cl.[7] .................................................. A61K 7/16
(52) U.S. Cl. ...................................... 424/49; 435/252.3
(58) Field of Search ........................ 424/49; 435/252.3; 514/12, 21, 900; 530/350, 356, 397, 399, 840

(56) References Cited

U.S. PATENT DOCUMENTS

| | | | |
|---|---|---|---|
| 4,472,840 A | * 9/1984 | Jefferies | 128/92 G |
| 4,877,864 A | 10/1989 | Wang et al. | 530/324 |
| 5,013,649 A | 5/1991 | Wang et al. | 530/350 |
| 5,024,841 A | 6/1991 | Chu et al. | 530/356 |
| 5,106,748 A | 4/1992 | Wozney et al. | 536/27 |
| 5,108,922 A | 4/1992 | Wang et al. | 536/27 |
| 5,116,738 A | 5/1992 | Wang et al. | 530/350 |
| 5,124,316 A | * 6/1992 | Antoniades et al. | 514/12 |
| 5,141,905 A | 8/1992 | Rosen et al. | 530/350 |
| 5,166,058 A | * 11/1992 | Wang et al. | 435/69.1 |
| 5,171,579 A | 12/1992 | Ron et al. | 424/486 |
| 5,187,076 A | 2/1993 | Wozney et al. | 530/350 |
| 5,197,882 A | 3/1993 | Jernberg | |
| 5,206,028 A | 4/1993 | Li | 424/484 |
| 5,256,418 A | 10/1993 | Kemp et al. | 530/356 |
| 5,324,519 A | * 6/1994 | Dunn et al. | 424/426 |
| 5,385,316 A | * 1/1995 | Yim et al. | 514/12 |
| 5,393,739 A | * 2/1995 | Bentz et al. | 514/12 |

FOREIGN PATENT DOCUMENTS

| | | |
|---|---|---|
| WO | WO 93/00050 | 1/1993 |
| WO | WO 93/09229 | 5/1993 |
| WO | WO 95/07108 | 3/1995 |

OTHER PUBLICATIONS

Graves, D., Periodontal Regeneration with Polypeptide Growth Factors, current Science 178–186, 1994.*
Database WPI, Section Ch, Week 9502, Derwent Publications Ltd., London, GB; Class B04, AN 95–010900 & JP,A,6 296 677 (Yamanouchi Pharm Co Ltd.) Oct. 25, 1994; See Abstract.

* cited by examiner

Primary Examiner—Ralph Gitomer
(74) Attorney, Agent, or Firm—Finnegan, Henderson, Farabow, Garrett & Dunner, LLP.

(57) ABSTRACT

Methods and compositions are provided for the treatment of periodontal disease and bone lesions. Preferred methods comprise administering a composition containing one or more osteogenic and/or ligament-inducing bone morphogenetic protein and a suitable carrier. The method results in the regeneration of alveolar bone in both a vertical and horizontal direction, and can result in the regeneration of bone, cementum and ligamentous structure between said regenerated bone and the tooth root surface, such that minimal ankylosis and root resorption results. The method and composition are useful for the repair of supraalveolar periodontal lesions and defects, mandibular and maxillary class II and III furcations and interproximal defects, and augmentation of the alveolar ridge of these structures.

18 Claims, No Drawings

METHODS FOR TREATMENT OF PERIODONTAL DISEASES AND LESIONS USING BONE MORPHOGENETIC PROTEINS

This application is a continuation-in-part of U.S. Pat. Ser. No. 08/208,722, filed on Mar. 8, 1994, which is presently abandoned.

FIELD OF THE INVENTION

The present invention relates to the field of tissue repair, specifically, the regeneration of a functional periodontal attachment apparatus destroyed by periodontitis. Specifically, the present invention relates to methods and compositions useful for the repair of periodontal defects, such as lesions involving the alveolar bone, periodontal ligament, and for the regeneration of cementum.

BACKGROUND OF THE INVENTION

Periodontal disease is a bacterially induced, host mediated, inflammatory disease that results in a loss of connective tissue attachment to the tooth and loss of alveolar bone. It is estimated that upwards of twenty-five percent of the population from 18 to 65 years old has some significant loss of connective tissue support at one or more sites. It is projected that nearly 10% of this population has attachment loss at multiple locations consistent with a diagnosis of moderate periodontitis.

Current periodontal disease therapies are directed at control of the inflammatory disease with the goal of preventing future disease. It is also desirable to seek to regenerate a functional periodontal attachment. To date, autogenous and allogeneic bone grafting has been the method most often used for defect filling and regeneration. However, other reconstructive surgical procedures, using synthetic alloplastic grafts or guided tissue regeneration with physical barriers are also performed.

Autogenous bone grafts are disadvantageous mainly in that they require surgery at a second site in order to obtain sufficient graft material, resulting in patient morbidity. Bone allograft may be obtained from tissue banks either fresh frozen or freeze-dried. Fresh tissue may be antigenic and is subject to limitations of current supply. Freeze-drying markedly reduces antigenicity of bone allograft, but may also decrease the osteogenic potential of the graft as well. Demineralization of the allograft may enhance osteogenic potential, but it decreases the structural integrity of the graft. In addition, the source is human donor bone which creates a risk of transmission of disease.

Alloplastic bone substitutes which have been tried include synthetic or natural hydroxyapatite, which is non-resorbable, beta tricalcium phosphate (resorbable) and polymer of polymethacrylate beads coated with polyhema bovine bone products. These materials tend to be encapsulated with minimal or no bone formation and also may cause root resorption. These bone substitutes may also cause ankylosis, and may not be suitable for regeneration of the cementum and of the periodontal ligament.

Guided tissue regeneration provides a physical barrier between the gum flap and the tooth surface to enhance the potential for wound healing. This procedure retards the apical migration of epithelium, excludes gingival connective tissue from the wound and favors healing from the periodontal ligament space. However, this procedure is technique- and site-sensitive, may leave space between the gum flap and tooth surface and does not reproducibly lead to repair of the periodontal defect.

Accordingly, despite substantial endeavors in this field, there remains a need for an effective method of repair of periodontal defects.

SUMMARY OF THE INVENTION

The present invention provides methods and compositions for regenerating periodontal tissue. In a particular embodiment, the present invention comprises methods of treating supraalveolar lesions, which have historically been difficult to treat because they involve both vertical and horizontal lesions of the alveolar bone. The methods and compositions of the present invention are advantageous in that they utilize osteogenic proteins and/or ligament-inducing proteins, which may be produced via recombinant DNA technology, and therefore are of potentially unlimited supply, and are not subject to the same concerns of contaminated source as are bone grafts. The methods and compositions of the present invention are further advantageous in that regeneration is begun of all three tissues comprising the periodontal attachment apparatus: alveolar bone, periodontal ligament space and cementum; which minimizes the occurrence of potentially undesirable conditions such as ankylosis and root resorption.

DETAILED DESCRIPTION OF THE INVENTION

According to the present invention, methods and compositions are provided for treatment of periodontal disease and for repair of periodontal lesions to the alveolar bone, particularly supraalveolar lesions which involve both vertical and horizontal lesions of the alveolar bone. Supraalveolar defects may affect areas in which the teet remain intact, in which case it is desirable to regenerate the entire periodontal attachment apparatus between alveolar bone and tooth. Alternatively, supraalveolar defects may affect areas in which the teeth have been lost, in which case it is desirable to augment the alveolar bone in order to allow more effective implantation of substitute teeth. In addition to supraalveolar defects, the methods and compositions of the present invention are useful for the treatment of mandibular and maxillary class II and III furcation and interproximal defects with and without bacterial involvement from periodontitis, as well as for ridge augmentation of both the mandibular and maxillary structures. Class II and III furcations and interproximal defects are subclasses of supraalveolar defects in which the teeth remain present. Ridge augmentation is often necessary when a patient has experienced substantial resorption of the mandibular and/or maxillary structures. This often occurs in patients who have been missing one or more teeth for an extended period of time.

The methods comprise applying to the site of a supraalveolar lesion, or to the site of a class II or class III furcation or interproximal defect, or to the mandibular or maxillary ridge requiring augmentation, an amount of a composition comprising one or more purified osteogenic and/or ligament-inducing proteins, which is effective to regenerate the alveolar mandibular and/or maxillary bone in both a vertical and horizontal direction. The methods and compositions are advantageous in that regeneration of the mandibular and/or maxillary bone in both a vertical and horizontal direction often results in bone which is better able to support dental implants. The methods and composition are further advantageous in that repair or improvement may be obtained of the entire periodontal attachment apparatus: the alveolar bone, the periodontal ligament space and the cementum layer. The method may further comprise the administration of a composition comprising a purified osteogenic and/or ligament-inducing protein to a site of periodontal lesion or defect in a suitable carrier such that the alveolar bone, the periodontal ligament apparatus, and the cementum layer are regenerated, without significant ankylosis and/or root resorption appearing. The composition is preferably administered in combination with an effective carrier. One of the key advantages of the method of the present invention is that it allows for the controlled regeneration of alveolar bone, periodontal ligament and cementum tissue in a manner which minimizes the occurrences of undesirable ankylosis and root resorption.

OSTEOGENIC OR LIGAMENT-INDUCING PROTEIN

The osteogenic protein is preferably from the subclass of proteins known generally as bone morphogenetic proteins (BMP), which have been disclosed to have osteogenic activity. These BMPs include BMP-2, BMP-4, BMP-5, BMP-6, BMP-7, BMP-8, BMP-9, BMP-10 and BMP-11 and may also include other members of the TGF-$\beta$ superfamily of proteins. The structures of a number of BMP proteins are disclosed in U.S. Pat. Nos. 4,877,864; 5,108,922; 5,013,649; 5,116,738; 5,106,748; 5,187,076; 5,141,905; and in PCT applications WO 91/18098; WO 93/00432; W094/26893; and W094/26892, the disclosures of which are hereby incorporated by reference. The preferred osteogenic protein is BMP-2, the sequence of which is disclosed in U.S. Pat. No. 5,013,649, the disclosure of which is hereby incorporated by reference. Other BMPs known in the art can also be used. The ligament-inducing protein is preferably also from the BMP subclass of the TGF-3 superfamily of proteins, but which have been disclosed to have tendon/ligament-like tissue inducing activity. These proteins include BMP-12, BMP-13 and MP52, and may also include other members of the TGF-$\beta$ superfamily of proteins. These proteins and their activity are described in U.S. patent application, Ser. No. 08/217,780, filed on Mar. 25, 1994, 08/333,576, filed on Nov. 2, 1994, and 08/362,670, filed on Dec. 22, 1994, the disclosures of which are hereby incorporated by reference. Presently, the most preferred osteogenic protein is BMP-2, and the most preferred ligament-inducing protein is BMP-12. In a preferred embodiment, both one or more osteogenic proteins and one or more ligament-inducing proteins as described above are used. The most preferred combination of osteogenic and ligament-inducing proteins is BMP-2 and BMP-12. The BMPs may be recombinantly produced, or purified from a protein composition. The BMPs may be homodimeric, or may be heterodimeric with other BMPs (e.g., a heterodimer composed of one monomer each of BMP-2 and BMP-6) or with other members of the TGF-$\beta$ superfamily, such as activins, inhibins and TGF-$\beta$1 (e.g., a heterodimer composed of one monomer each of a BMP and a related member of the TGF-$\beta$ superfamily). Examples of such heterodimeric proteins are described for example in Published PCT Pat. Application WO93/09229, the specification of which is hereby incorporated herein by reference. In a preferred embodiment, the protein is a heterodimer of an osteogenic BMP, such as BMP-2, and a ligament-inducing BMP, such as BMP-12. The amount of osteogenic protein useful herein is that amount effective to stimulate increased osteogenic activity of infiltrating progenitor cells, and will depend upon the size and nature of defect being treated, as well as the carrier being employed. Similarly, the amount of ligament-inducing protein useful herein is that amount effective to stimulate increased ligament-forming activity of progenitor cells, and will depend upon the size and nature of the defect, as well as the carrier. Generally, the amount of either protein to be delivered is in a range of from about 0.05 to about 1.5 mg per cc or ml of carrier. In the embodiment wherein both an osteogenic protein and a ligament-inducing protein are employed, the proteins are preferably employed in a ratio of from about 90:10 to 10:90 percent osteogenic protein:ligament-inducing protein; most preferably in a ratio from about 60:40 to about 40:60.

CARRIER

Materials which may be useful as the carrier in practicing the present invention include pharmaceutically acceptable materials having viscosity and polarity such that, when added to the bone morphogenetic protein, form a composition that possesses appropriate handling characteristics (i.e., is neither too runny to remain at the defect or lesion site nor too firm so as not to be moldable) for application to the site of periodontal disease or lesion. Adding the carrier to the bone morphogenetic protein allows the protein to remain in the disease or lesion site for a time sufficient to allow the protein to increase the otherwise natural rate of regenerative osteogenic activity of the infiltrating mammalian progenitor cells, and to form a space in which new tissue can grow and to allow ingrowth of cells. The carrier may also allow the bone morphogenetic protein to be released from the lesion, defect or disease site over a time interval appropriate for optimally increasing the rate of regenerative osteogenic and ligament-forming activity of the progenitor cells.

A preferred family of carriers for administration of the bone morphogenetic proteins are porous particulate polymers, described in detail in U.S. Pat. No. 5,171,579, the entire disclosure of which is incorporated herein by reference. The protein and polymers are preferably sequestered by a sequestering agent, such as autologous blood. An alternative carrier useful for the present invention is a formulation of osteogenic protein, porous particulate polymers and another sequestering agent, such as cellulosic material. Other preferred sequestering agents include hyaluronic acid, sodium alginate, poly(ethylene glycol), polyoxyethylene oxide, carboxyvinyl polymer and poly(vinyl alcohol). Most preferred as the sequestering agent for this embodiment is carboxymethylcellulose. These compositions are described in the published PCT application WO 93/00050, the entire disclosure of which is hereby incorporated herein by reference. The cellulosic protein sequestering agent is preferably present in a concentration of about 1 to about 10% (w/v implant). The porous particulate polymer/cellulosic sequestering agent may optionally be further combined with aqueous glycerol as a diluent, preferably in concentrations of about 10 to about 80% (v/v); and ratios of sequestering agent/liquid solution:porous particulate polymers are preferably from about 0.1 to about 0.9 (v/v). The amount of osteogenic and/or ligament-inducing protein used with porous particulate polymers is generally in the range of 0.01 to 1 mg of protein, preferably 0.05 to 0.6 mg protein for each cubic centimeter of composition employed.

Another preferred family of carriers is collagenous materials. Suitable collagen materials include Collastat® and Helistat® collagen sponges (Integra LifeSciences Corp., Plainsboro, N.J.). Other collagen materials which may be suitable for use in the present invention are described in U.S. Pat. Nos. 5,206,028; U.S. Pat. No. 5,024,841; U.S. Pat. No. 5,256,418. The collagen carrier is preferably in the form of a sponge. The collagen sponge may be loaded with protein prior to administration by soaking the sponge in the desired volume and concentration of protein for a suitable time period. The collagen sponge is preferably soak loaded with protein in a range from about 10% to about 150% v/v [ml protein/cc dry sponge], more preferably about 10 to about 60% v/v. Alternatively, the protein may be adsorbed to the collagen sponge during production. In this case, bone morphogenetic protein is preferably added to the collagen sponge during production and lyophilized to form a unitary product. The protein is preferably added in a ratio of from about 10 to about 150% v/v, more preferably in a range from about 60 to about 80% v/v.

Another preferred family of carriers is cellulosic materials such as alkylcellulose (including hydroxyalkylcellulose), including methylcellulose, ethylcellulose, hydroxyethylcellulose, hydroxypropylcellulose, hydroxypropyl-methylcellulose, and carboxymethylcellulose, the most preferred being the cationic salts of carboxymethylcellulose (CMC).

In the case of cellulosic carriers, it is preferred that the carrier be in the form of a hydrated cellulosic viscous gel. Viscosity of cellulosic materials may be increased through mechanical means, such as high agitation for a suitable period of time, followed by autoclaving. The bone morphogenetic protein and cellulosic carrier is in a solution of suitable buffer. One preferred buffer solution is a composition comprising, in addition to the osteogenic and/or ligament-inducing protein, about 1.0 to about 10.0% (w/v) glycine, about 0.1 to about 5.0% (w/v) of a sugar, preferably sucrose, about 1 to about 20 mM glutamic acid hydrochloride, and optionally about 0.01 to about 0.1% of a non-ionic surfactant, such as polysorbate 80. Preferred solutions are from about 1% to about 20% w/v cellulosic carrier/buffer. If desired, a salt may be added. A preferred viscous gel carrier is described in Example 2 below. The amount of osteogenic and/or ligament-inducing protein useful with viscous gel carrier is generally in a range of from about 0.05 to about 1.5 mg, preferably from about 0.1 to about 1.0 mg per cubic centimeter of implant material required.

Other materials which may be suitable for use as carriers for bone morphogenetic proteins in the methods and compositions of the present invention include demineralized bone, and minerals and ceramics, such as calcium phosphates, hydroxyapatite, etc. Other potential carriers include carriers for injectable formulations of BMPs. Suitable carriers for injectable formulations include, for example, soluble collagen, hyalouronic acid, polylactic acid/polyethylene glycol, and polymers.

The following examples further describe the practice of embodiments of the invention with BMP-2 in a porous particulate polymer carrier (Example 1) and in collagen sponge and viscous gel carriers (Example 2). The examples are not limiting, and as will be appreciated by those skilled in the art, can be varied in accordance with the above specification.

EXAMPLES

Example 1

BMP-2 and Porous Particulate Polymer Carrier in Surgically Created Defects

Surgical procedures and histometric analysis were performed in accordance with published techniques. See, for example, Wikesjö, *Periodontal Repair in Dogs: Connective Tissue Repair in Supraalveolar Periodontal Defects*, Loma Linda University (1991). Surgical procedures were performed under intravenous sodium pentobarbital anesthesia. The dogs also received intravenous lactated Ringer's solution and were fed a soft consistency laboratory diet supplemented with vitamins throughout the experiment.

Six male beagle dogs, 18 to 24 months old, were used. Routine supraalveolar periodontal defects were created around the 2nd, 3rd and 4th mandibular premolar teeth. Briefly, following sulcular incisions and elevation of buccal and lingual mucoperiosteal flaps, alveolar bone was surgically removed around the full circumference of the teeth. Clinical defect height from the cemento-enamel junction to the reduced alveolar crest was determined to 5 mm. The crowns of the teeth were reduced to 1 mm above the cemento-enamel junction and exposed pulps sealed. The 1st mandibular premolar was extracted and the crown of the 1st molar amputated at the level of the surgically reduced alveolar crest.

Implants consisting of sterile rhBMP-2 and autologous blood plus particles of porous polylactic acid/polyglycolic acid copolymer [50:50] were formulated at a dose of 20 $\mu$g rhBMP-2/100 $\mu$l implant volume. A device volume of 5 ml (2.5 to 3 mL implanted volume) was prepared for experimental defects. Control defects received buffer formulated with autologous blood and particles, but no BMP-2.

Surgically exposed root surfaces were instrumented to remove the cementum. Supraalveolar premolar teeth defects in alternate quadrants in subsequent dogs were randomly assigned to be treated with BMP-2 or vehicle control. The implants were molded around the premolar teeth. Periostea were then fenestrated at the base of the flaps, and the flaps advanced to submerge the implant covered teeth. Flaps were sutured with mattress sutures [Gore-Tex Suture CV5, WL Gore & Associates, Inc. AZ] which were removed 2 weeks post-surgery. A long acting opiate was administered twice daily the first 2 weeks post-surgery for infection control. Plaque control was accomplished by a daily 2% chlorhexidine rinse.

Clinical Observations

Primary wound closure was obtained in all dogs. At suture removal 2 weeks post-surgery, there was an obvious difference in tissue mass between jaw quadrants for each dog. Contours of the submerged teeth could easily be recognized in control quadrants. In BMP-2 quadrants, the tissue had increased significantly necessitating reduction of opposing teeth to prevent trauma to the surgical sites. The tissue mass was firm to palpation.

Radiographic Observations

Radiographs were exposed with films placed extraorally at 2 and 4 weeks post-surgery. At sacrifice (8 weeks post-surgery), radiographs were obtained after the jaws had been removed and sectioned through the mid-line, improving the angle of exposure and eliminating the image of contralateral teeth.

Two week observations exhibited radiopacity in rhBMP-2 quadrants. In general, the area of radiopacity paralleled that observed at 2 weeks. Control quadrants exhibited an apparent decrease in radiopacity; only localized areas exhibited minor increases in radiopacity.

Eight week observations exhibited continued increased radiopacity in rhBMP-2 quadrants with an appearance of trabecular bone and a lamina dura continuous with the reduced alveolar bone. The radiopacity completely filled the surgically created defects. Control quadrants exhibited limited, if any, evidence of regeneration of mineralized structure.

Histologic Observations

Histologic observations revealed extensive bone regeneration in rhBMP-2 quadrants. Frequently, the newly formed bone extended coronal to the cemento-enamel junction, at times completely covering the teeth. Bone trabeculae were lined with osteoblast-like cells. A dominating feature of the new bone was wide marrow spaces with only sparse cell structures. A periodontal space was observed between the instrumented roots and the newly formed bone. Periodontal regeneration was substantiated by cementum regeneration (a thin layer of cementum or cementum-like deposit on the root surface). Mean cementum regeneration approximated 40% of the defect height. The cementum was expressed as a continuous layer from the base of the defects, variably covering the roots, above which isolated cementum islands appeared randomly. Limited root resorption was observed. Root resorption was significantly reduced in rhBMP-2 treated defects compared to controls. Ankylosis, when present, generally was limited to immediately apical to the cemento-enamel junction. Since few control defects exhibited bone regeneration approaching that level, only a few controls exhibited ankylosis.

Control quadrants exhibited limited bone regeneration. However, a few teeth displayed bone regeneration approaching the cemento-enamel junction, including localized ankylosis as observed in rhBMP-2 quadrants. Cementum regeneration was limited, whereas root resorption was observed over larger areas of the roots.

Because the present studies were terminated at an 8 week time point, periodontal ligament regeneration is defined as substantiated by the formation of periodontal ligament space and precursor collagenous structure orientation to periodontal ligament. It is anticipated that follow-up studies extending healing time will provide further support for the regeneration of periodontal ligament.

Histometric Observations

The results from the histometric analysis are shown in Table 1. One rhBMP-2 treated premolar tooth defect was lost in histologic processing. The exposed control tooth defect was also excluded from analysis.

The following measurements were recorded for the buccal and lingual surfaces of each root for each section. Mean averages and standard deviations for all measurements are shown in Table 1:

Defect Height: distance between apical extension of root planing and cemento-enamel junction.

Bone Regeneration (height): distance between apical extension of root planing and coronal extension of regenerated alveolar bone along the root.

Bone Regeneration (area): cross-sectional area represented by regenerated alveolar bone along the root.

Cementum Regeneration: distance between apical extension of root planing and coronal extension of continuous layer of regenerated cementum or cementum-like deposit on the root.

Root Resorption: combined linear heights of distinct resorption lacunae on the root.

Ankylosis: combined linear heights of ankylotic union of regenerated alveolar bone and the root.

Mean and standard deviation for each measurement were calculated per tooth (4 root surfaces/tooth) and dog using selected step serial sections. Differences between treatments were analyzed using Student's t-test for paired observations (N=6). A P-value of <0.05 is considered to be statistically significant. Additionally, frequencies of teeth presenting with cementum regeneration, root resorption and ankylosis were calculated. Presence of these features in 1 or more of the 6 sections from each tooth resulted in a positive score for the tooth.

TABLE 1A

Periodontal Healing Following Reconstructive Surgery and Wound Conditioning With rhBMP-2 or Vehicle Control in Supraalveolar Periodontal Defects in Beagle Dogs

|  | rhBMP-2 | Control | P-Value |
|---|---|---|---|
| Defect Height | 3.7 ± 0.3 | 3.9 ± 0.4 | 0.446 |
| Bone Regen (Ht) | 3.5 ± 0.6 | 0.8 ± 0.6 | 0.000 |
| Bone Regen (Area) | 8.4 ± 4.5 | 0.4 ± 0.5 | 0.006 |
| Cementum Regen | 1.6 ± 0.6 | 0.4 ± 0.3 | 0.005 |
| Root Resorption | 0.2 ± 0.1 | 1.1 ± 0.3 | 0.001 |
| Ankylosis | 0.8 ± 0.6 | 0.1 ± 0.1 | 0.025 |

Bone regeneration above does not include bone regeneration coronal to the cemento-enamel junction. Such regeneration was also evaluated:

TABLE 1B

|  | rhBMP-2 | Control | P-Value |
|---|---|---|---|
| Bone Regen (Ht) | 1.7 ± 1.4 | 0.0 ± 0.0 | 0.014 |
| Bone Regen (Area) | 2.2 ± 2.4 | 0.0 ± 0.0 | 0.039 |

The above results prove the efficacy of rhBMP-2 in suitable carrier in regeneration of not only bone, but also periodontal regeneration substantiated by cementum regeneration. Further, these studies show significant efficacy in treatment of supraalveolar lesions, which involve both vertical and horizontal lesions of the alveolar bone. These results are significantly more promising than any current therapy or potential treatment modality previously examined in animal models.

Example 2

BMP in Collagen Sponge and Viscous Gel Carriers to Treat Surgically Created and Naturally Occurring Advanced Periodontal Disease Defects.

Ten mature beagle dogs with naturally-occurring advanced class II or class III periodontal disease defects in premolar 4 and molar 1 and induced defects in premolars 2 and 3 through bone resection followed by ligature.

Subjects are treated with Collastat® collagen sponge hydrated with rhBMP-2 or vehicle control; or a viscous gel combined with rhBMP-2, or vehicle control. Collagen sponge is prepared as follows: rhBMP-2 solution is made by adding 0.93 mL water for injection to each vial of rhBMP-2 to a final concentration of 5 mg/mL. 1:15 dilution of 0.7 mL BMP stock into pre-aliquoted 9.5 mL buffer vials gives a working dilution of 0.34 mg/mL. 8×50×5mm collagen sponges, 2 mL dry sponge volume, are wetted with 1.2 mL of 0.34 mg/mL stock, giving a final dose of 20 $\mu$g/100 $\mu$L of implant material. 3 sponges are used per quadrant.

Viscous gel is prepared as follows: 5% (CMC/buffer) CMC 7HF (Aqualon) is prepared by rehydrating the CMC in buffer solution at high agitation for an extended period of time. Green food coloring was added to aid in visualization of material placement in the surgical field. 3 mL aliquots were transferred to 10 mL vials and autoclaved. 0.6 mL of rhBMP-2 stock (5 mgBMP-2/mL) is added to each CMC vial and stirred. A final dosage of 0.8 mg rhBMP-2/mL of viscous gel is achieved. 1 ml of viscous gel is used for each quadrant.

The buffer solution for the viscous gel comprises 2.5% (w/v) glycine, 0.5% (w/v) sucrose, 0.01% (w/v) polysorbate 80 and 5 mM (about 0.092% (w/v)) glutamic acid HCl; at pH=4.5.

The subjects are randomized as described in Table 2:

TABLE 2

| ANIMAL | RIGHT MANDIBULAR QUADRANT | LEFT MANDIBULAR QUADRANT |
|---|---|---|
| 1 | Collastat (2X) | VG (8X) |
| 2 | Collastat (2X) | Collastat (Control) |
| 3 | VG (Control) | Collastat (BMP-2) |
| 4 | Surgical Control | Collastat (BMP-2) |
| 5 | Collastat (Control) | VG (BMP-2) |
| 6 | Collastat (Control) | VG (Control) |
| 7 | Surgical Control | Collastat (Control) |
| 8 | VG (8X) | Surgical Control |
| 9 | VG (8X) | VG (Control) |
| 10 | VG (Control) | Surgical Control |

KEY:
Collastat (2X): 20 μg rhBMP/-2/100 μL Collastat ® sponge implant
Collastat (Control): Collastat ® sponge with no BMP
VG (8X): 80 μg rhBMP-2/100 μL implant CMC viscous gel
VG (Control): CMC viscous gel with no BMP
Surgical Control: No implant The results are evaluated clinically, radiographically and histometrically, as performed in Example 1 above.

We claim:

1. A method for treatment of a supraalveolar periodontal lesion or defect comprising administering to said lesion or defect a pharmaceutically acceptable admixture of a suitable carrier and bone morphogenetic protein-12 ((BMP-12) in an amount sufficient to cause regeneration of alveolar bone or periodontal ligament at the site of said lesion or defect.

2. A method according to claim 1, wherein the carrier comprises a collagen sponge.

3. A method according to claim 1, wherein the carrier comprises a cellulosic viscous gel.

4. A method according to claim 1, wherein the carrier comprises porous particulate polymers and a sequestering agent.

5. A method according to claim 4, wherein the sequestering agent is autologous blood.

6. A method according to claim 4, wherein the sequestering agent is a cellulosic material.

7. A method for treatment of mandibular or maxillary class II and III furcation or interproximal defects with or without bacterial involvement for periodontis, said method comprising applying to said defect a pharmaceutically acceptable admixture of suitable carrier and bone morphogenetic protein (BMP-12) in an amount sufficient to cause regeneration within said furcation or defect of bone, cementum, and ligamentous structure between said regenerated bone and the tooth root surface.

8. A method according to claim 7, wherein the carrier comprises a collagen sponge.

9. A method according to claim 7, wherein the carrier comprises a cellulosic viscous gel.

10. A method according to claim 7, wherein the carrier comprises porous particulate polymers and a sequestering agent.

11. A method according to claim 10, wherein the sequestering agent is autologous blood.

12. A method according to claim 10, wherein the sequestering agent is a cellulosic material.

13. A method for augmentation of the mandibular or maxillary alveolar ridge, said method comprising applying to said ridge a pharmaceutically acceptable admixture of a suitable carrier and bone morphogenetic protein-12 (BMP-12) in an amount sufficient to cause regeneration of alveolar bone at said alveolar ridge.

14. A method according to claim 13, wherein the carrier comprises a collagen sponge.

15. A method according to claim 13, wherein the carrier comprises a cellulosic viscous gel.

16. A method according to claim 13, wherein the carrier comprises porous particulate polymers and a sequestering agent.

17. A method according to claim 16, wherein the sequestering agent is autologous blood.

18. A method according to claim 16, wherein the sequestering agent is a cellulosic material.

* * * * *